United States Patent
Fukuda et al.

(10) Patent No.: US 6,232,294 B1
(45) Date of Patent: May 15, 2001

(54) NEURO-FUNCTION REGULATORY AGENT

(75) Inventors: Shigeharu Fukuda; Toshio Miyake, both of Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 0 days.

(21) Appl. No.: 09/206,692

(22) Filed: Dec. 7, 1998

(30) Foreign Application Priority Data

Dec. 9, 1997 (JP) .................................................... 9-354068
Nov. 11, 1998 (JP) .................................................. 10-320778

(51) Int. Cl.⁷ .................................................... A61K 31/70
(52) U.S. Cl. .................................. 514/42; 514/25; 514/34
(58) Field of Search .................................... 514/42, 25, 34

(56) References Cited

U.S. PATENT DOCUMENTS 4,211,772   7/1980   Fauran et al. .
5,702,727 * 12/1997   Amkraut et al. .

FOREIGN PATENT DOCUMENTS

0420376   * 9/1989   (EP) .
0 387 042      9/1990   (EP) .
0387042        9/1990   (EP) .
0480640   * 10/1990   (EP) .
0 402 049     12/1990   (EP) .
0402049       12/1990   (EP) .
0 420 376      4/1991   (EP) .
0 480 640      4/1992   (EP) .
0 486 315      5/1992   (EP) .
0565313       10/1993   (EP) .
0628630   * 12/1994   (EP) .
0 628 630     12/1994   (EP) .
0 671 470      9/1995   (EP) .
0 674 005      9/1995   (EP) .
0 688 866     12/1995   (EP) .
0 688 867     12/1995   (EP) .
0 691 344      1/1996   (EP) .
0 693 558      1/1996   (EP) .
0691344   *  1/1996   (EP) .
0 697 461      2/1996   (EP) .
0 704 531      4/1996   (EP) .
0 709 461      5/1996   (EP) .

* cited by examiner

Primary Examiner—James O. Wilson
(74) Attorney, Agent, or Firm—Browdy & Neimark

(57) ABSTRACT

A neuro-function regulatory agent with lesser side effects, comprising glycosyl vitamin P as an effective ingredient. When administered to patients with nerve diseases, the agent exerts a remarkable effect on the relief of patients' symptoms accompanied by nerve diseases.

14 Claims, No Drawings

NEURO-FUNCTION REGULATORY AGENT

BACKGROUND OF THE INVENTION

1. Field of the Invention

The present invention relates to a neuro-function regulatory agent, and more particularly to a neuro-function regulatory agent comprising glycosyl vitamin P as an effective ingredient.

2. Description of the Prior Art

The nervous system consists of nerve cells and fibers, has abilities of accepting and transmitting excitations, and keeps the homeostasis between individual activities and functional correlations in various parts of the body through a specific and highly-complicated neuronetwork. Disorder or disturbance of the neuro-function results in abnormal symptoms of physical and perception abilities and of circulatory and digestive organs, and may cause diseases including nerve diseases if such disorder or troublesome is being continued. Therefore keeping the neuro-function within the normal condition is very important for busy modern humans to spend their lives comfortably and to prevent them from nerve diseases. However, conventionally proposed methods for preventing nerve diseases are merely teachings of daily life such as taking care of living on well-balanced foods and of having regular habits while avoiding excessive stimuli, stresses, and fatigues as mush as possible.

SUMMARY OF THE INVENTION

In view of the foregoing, the object of the present invention is to provide a daily-usable means for effectively regulating the neuro-function with lesser side effects.

The present inventors studied vitamins to solve the above object. As a result, they elucidated the fact that glycosyl vitamin P exerts an unexpected action; it regulates the neuro-function to the desired condition or the normal condition when administered to humans, and found that the action of glycosyl vitamin P is significantly accelerated by trehalose, a disaccharide. Thus the present invention solves the above object by providing a neuro-function regulatory agent comprising glycosyl vitamin P as an effective ingredient.

The glycosyl vitamin P used in the present invention is a known compound, and similarly as vitamin P it is known that the compound has an activity of inhibiting the permeability of capillaries. The present invention was made based on an unexpected finding that the action of glycosyl vitamin P that regulates the human neuro-function independently of the inhibition of capillary permeability. The present invention is novel in that it provides a use of glycosyl vitamin P as a neuro-function regulatory agent.

DETAILED DESCRIPTION OF THE INVENTION

The present invention relates to a neuro-function regulatory agent comprising glycosyl vitamin P as an effective ingredient. The glycosyl vitamin P used in the present invention generally includes glycosyl hesperidins such as a series of α-monoglucosyl hesperidin, α-diglucosyl hesperidin, α-triglucosyl hesperidin, α-tetraglucosyl hesperidin, and α-pentaglucosyl hesperidin; and glycosyl rutins such as a series of α-monoglucosyl rutin, α-diglucosyl rutin, α-triglucosyl rutin, α-tetraglucosyl rutin, and α-pentaglucosyl rutin. Since these compounds exert substantially the same level of activity of regulating the neuro-function, the present agent should contain one or more of them in an effective amount in total. In this connection, glycosyl hesperidins are superior to glycosyl rutins when compared with their activities on improving nerve disorder or disturbance and on preventing nerve diseases.

The glycosyl vitamin P can be prepared by various methods. With an economical viewpoint, biochemical methods with saccharide-transferring enzymes are advantageous; The aforesaid series of glycosyl vitamin P can be obtained in a relatively-high yield by contacting vitamin P such as hesperidin and rutin with saccharide-transferring enzymes such as α-glucosidase, cyclomaltodextrin glucanotransferase, and α-amylase in the presence of α-glucosyl saccharides such as partial starch hydrolysates and maltooligosaccharides. The reaction products thus obtained usually contain a series of glycosyl vitamin P compounds with glucose polymerization degrees of 1–5 or more in terms of transferred glucoses. These compounds can be hydrolyzed into α-monoglucosyl vitamin P by the action of glucoamylase and optionally in combination with rhamnosidase. Methods using saccharide-transferring enzymes are disclosed in detail in Japanese Patent Kokai Nos. 7,593/91, 27,293/91, 58,790/91, 115,292/91, and 70,994/98 applied by the same applicant as the present invention; and Japanese Patent Application Nos. 22,667/97, and 63,396/98, an application based on a priority of Japanese Patent Application No. 69,588/97 by the same applicant as the present invention. Examples of commercialized products prepared by these methods are "αG RUTIN", a powdery glycosyl rutin product with a total rutin content of 40–82%, on a dry solid basis (d.s.b.), commercialized by Hayashibara Shoji, Inc., Okayama, Japan; and "αG HESPERIDIN", a powdery glycosyl hesperidin product with a total hesperidin content of 22–84%, d.s.b., commercialized by Hayashibara Shoji, Inc., Okayama, Japan. The glycosyl vitamin P used in the present invention should not necessarily be those in a highly-purified form and can be those in the form of a composition unseparated from other substances formed depending on the preparation methods used.

As described above, the activity of regulating the neuro-function by glycosyl vitamin P is significantly augmented by coexisting trehalose, which trehalose also stabilizes the glycosyl vitamin P, facilitates the administration of the compound, and exerts an activity of promoting the absorption of the compound. Since there found no natural system where glycosyl vitamin P coexists with trehalose, the fact that trehalose promotes the effective activities of glycosyl vitamin P was nothing but a completely-unpredictable finding. The present embodiment using an artificial combination of an artificially-produced glycosyl vitamin P and trehalose is quite novel at this point.

Explaining the trehalose advantageously usable in the present invention, there found, as it is well known, three types of isomers called α,αα-, α,β-, and β,β-isomers with different bonding forms. Since these isomers exert a similar promoting activity on glycosyl vitamin P, they can be used in the present agent for regulating the neuro-function independently of their preparation, purity, and property as long as one or more of them are incorporated into the present agent in an effective amount in total.

Trehalose can be produced by various methods. Detailed descriptions of such methods are given up because this invention in itself does not relate to the same. However, considering economical benefit, preferable methods are those which comprise of contacting partial starch hydrolysates with a non-reducing saccharide-forming enzyme and a trehalose-releasing enzyme as disclosed in Japanese Patent Kokai Nos. 143,876/95, 213,283/95, 322,883/95, 298,880/

95, 66,187/96, 66,188/96, 336,388/96, and 84,586/96. According to these methods, a,α-trehalose can be produced from starches as costless materials in a relatively-high yield; Examples of commercialized products obtainable thereby are "TREHAOSE®", a crystalline trehalose powder containing at least 98% trehalose, d.s.b., commercialized by Hayashibara Shoji, Inc., Okayama, Japan; and "TREHASTAR®", a trehalose syrup containing at least 28% trehalose, d.s.b., commercialized by Hayashibara Shoji, Inc., Okayama, Japan. α,α-Trehalose can be produced by contacting partial starch hydrolysates either with a maltose/trehalose converting enzyme as disclosed in Japanese Patent Kokai Nos. 149,980/96 and 9,986/97 or with conventionally known maltose-and trehalose-phosphorylases in combination.

To produce α,β-trehalose, cyclomaltodextrin glucanotransferase, and β-galactosidase are allowed in this order to contact with mixtures of partial starch hydrolysates and lactose according to the methods as disclosed in Japanese Patent Kokai Nos. 144,694/92 and 179,490/92 applied by the same applicant as the present invention. Similarly as glycosyl vitamin P, the trehalose used in the present invention should not necessarily be those in a highly-purified form or may be those in the form of a composition unseparated from other particular substances formed depending on the preparation methods used. Depending on use, the present agent contains trehalose in an amount of at least five-fold higher, and preferably 50-fold or higher than that of glycosyl vitamin P, d.s.b.

The agent according to the present invention includes those which consist of glycosyl vitamin P and those in the form of compositions comprising glycosyl vitamin P and another ingredients that ease the administration of glycosyl vitamin P. The above compositions are usually commercialized in the form of a liquid, paste or solid food product or pharmaceutical. The agent in the form a food product can be prepared into a composition comprising materials and/or ingredients used generally in food products such as water, alcohols, amylaceous substances, fibers, saccharides, lipids, fatty acids including essential fatty acids, vitamins including ascorbic acid and glycosyl ascorbic acids, minerals including salts of magnesium and calcium, herb medicines including rikkunshi-to, hochu-ekki-to, flavors, coloring agents, sweeteners, seasonings, stabilizers, and preservatives. The agent in the form a pharmaceutical can be formulated in a composition comprising carriers, excipients, adjuvants, diluents, and stabilizers, and optionally one or more of another ingredients, which are generally used in the treatment of nerve diseases, such as psycho- and nerve-agents, autonomic nerve agents, and sensory organs' agents, as well as the above mentioned lipids, vitamins, minerals, and herb medicines, and interferons including interferon-α. Independently of the aforesaid forms, the present agent usually contains glycosyl vitamin P in an amount of at least 0.001 w/w %, and preferably 0.01–10 w/w %. As already explained, trehalose effectively facilitates the administration of glycosyl vitamin P.

Explaining the use of the present agent for regulating the neuro-function, it exerts a remarkable activity of regulating the neuro-function independently of the oral- and parenteral-administrations. Depending on use, in the case of maintaining/promoting the normal neuro-function and preventing nerve diseases, the present agent is usually administered orally in the form of a food product, while in the case of treating nerve diseases and of recovering the desired neuro-function, the present agent is usually administered orally in the form of a pharmaceutical or food product, or administered parenterally in the form of an injection or external medicament. The dose of the present agent is about 0.1 mg to about 10 g per shot per adult, and preferably one milligram to one gram per shot per adult in terms of glycosyl vitamin P at an administration frequency of 1–20 shots/day or at a prescribed time interval of several days.

The diseases applicable for the use of the present neuro-function regulatory agent are, for example, nerve diseases in general including depression, neurosis, Méniére's disease, neurasthenia, chronic fatigue syndrome, nervous digestive-diseases, nervous gastritis, and autonomic dystonia. When administered to patients with these diseases, the present agent exerts a remarkable effect on relieving loss of appetite, insomnia, emotional disturbance, malaise, ease feeling to fatigue, feeling of anxiety, emotional instability, ataxia, paresthesia, lalopathy, paralysis, headache, dizziness, nausea, diarrhea, palpitation, muscle stiffness of the shoulder, lumbago, etc. The present agent also exerts a remarkable effect on relieving feeling of fatigue, malaise, ease feeling to fatigue, loss of appetite, insomnia, and loss of vitality. Thus the present agent exerts characteristic effects in a manner such that it acts on neuro-functional disorder or disturbance to orientate the neuro-function to the desired normal condition by administering to patients with such troublesome, while the agent orientates the normal neuro-function to be maintained or even accelerated by administering to healthy persons.

Based on the following experiments, the effect and safety of the present agent are described as follows:

Experiment 1

Clinical Test

A clinical test was experimented using 50 volunteers, ages of 24–73, diagnosed with chronic fatigue syndrome or slight depression; Five groups consisting of randomly chosen 10 volunteers from the 50 volunteers were provided, and while observing the volunteers's conditions, they were orally administered every day and every after meals for a maximum period of one month with three tablets of either of a tablet as a specimen No. 1, prepared by the method in the later described Example 5; a tablet as a specimen No. 2 similarly prepared by the method in Example 5 except for replacing the glycosyl hesperidin powder with an equal amount of "αG RUTIN PS" having a total rutin content of 80–82%, d.s.b., a glycosyl rutin powder commercialized by Hayashibara Shoji, Inc., Okayama, Japan; a tablet as a specimen No. 3 similarly prepared by the method in Example 5 except for replacing the crystalline trehalose powder with an equal amount of sucrose; a tablet as a specimen No. 4 similarly prepared by the method in Example 5 except for replacing the glycosyl hesperidin powder with an equal amount of "αG RUTIN PS", having a total rutin content of 80–82%, d.s.b., a glycosyl rutin powder commercialized by Hayashibara Shoji, Inc., Okayama, Japan, and replacing the crystalline trehalose powder with an equal amount of sucrose; or a placebo as a control similarly prepared by the method in Example 5 except for omitting the glycosyl hesperidin powder. A medical technologist conducted the clinical experiment and 24 hours after the final administration asked the therapeutic effect and the side effects of the volunteers, and also asked the therapeutic effect and side effects of the volunteers on the basis of the relief of feeling of fatigue, malaise, loss of appetite, and insomnia, which were accompanied by the diseases. The therapeutic effect was evaluated based on four ranks; "very effective", "effective", "unchanged", and "worsened". The effectivity was expressed by a percentage of the number of volunteers, who answered "very effective" and "effective", to the total number of volunteers. The results are in Table 1:

TABLE 1

| Judgement | Specimen No. | | | | Control |
|---|---|---|---|---|---|
| | 1 | 2 | 3 | 4 | |
| Very effective | 3 | 1 | 2 | 0 | 0 |
| Effective | 5 | 4 | 4 | 4 | 1 |
| Unchanged | 2 | 4 | 4 | 5 | 8 |
| Worsened | 0 | 1 | 0 | 1 | 1 |
| Effectivity (%) | 80 | 50 | 60 | 40 | 10 |

The results in Table 1 show that glycosyl vitamin P is effective on chronic fatigue syndrome and slight depression, and that glycosyl hesperidin is superior to glycosyl rutin. The above-mentioned chronic fatigue syndrome and slight depression, which are typical ones of disorder and disturbance of neuro-function induced by social, physical-, and chemical-stresses that are found frequently in relatively younger and elder ages. The fact that glycosyl vitamin P effectively relieved these symptoms evidences that the present neuro-function regulatory agent has activities of maintaining the neuro-function of healthy persons and patients with nerve diseases within the normal condition and of restoring the neuro-function in disordered and disturbed conditions to the normal condition. A preliminary experiment on patients with nervous digestive-diseases other than chronic fatigue syndrome and slight depression resulted in a relief of gastrointestinal asthenia, constipation, diarrhea, etc. The result indicates an effectivity of the present agent. Through an experiment conducted similarly as with vitamin P, no significant effect was found as compared with control, and this would conclude that an effective amount of vitamin P did not absorbed by the body due to its relatively-low water solubility.

Experiment 2

Acute Toxicity Test

An adequate amount of "TREHAOSE®", a crystalline trehalose powder commercialized by Hayashibara Shoji, Inc., Okayama, Japan, was dissolved in physiological saline containing 5 w/w % gum arabic, and the solution was sterilized in usual manner and intraperitoneally injected to ddy-mice, 20–25 g weight, in a group of 10 mice, or orally administered to the mice by using a stomach sonde. Thereafter, the mice were observed for a week. As a result, no mouse died even administered with a dose of about 16 g per kg mouse as a maximum dose challenged, independently of its administration route. In parallel similar experiments were conducted using as glycosyl vitamin P "αG HESPERIDIN PA" with a total hesperidin content of 74–78%, d.s.b., a glycosyl hesperidin power commercialized by Hayashibara Shoji, Inc., Okayama, Japan, and "αG RUTIN PS" with a total rutin content of 80–82%, d.s.b., a glycosyl rutin powder commercialized by Hayashibara Shoji, Inc., Okayama, Japan. As a result, no mouse died up to a dose of about five grams per kg mouse as a maximum dose challenged.

The results in Experiments 1 and 2 evidence that the present neuro-function regulatory agent is effectively administered to humans with lesser side effects.

The following are the preferred examples of applications of the present neuro-function regulatory agent:

Example of Application 1

Neurosis

A 36-year-old male patient, who was diagnosed with neurosis and has been suffering from headache, dorsal pain, lumbodynia, and malaise as main symptoms, was administered with a supplemental health food as an example of the present agent for regulating the neuro-function (designated as "the supplemental health food" in Examples for application 1 to 3), prepared by the method in the later described Example 4, at a dose of about one gram per shot and an administration frequency of up to 10 shots per day. The administration frequency was allowed for the conditions of the patient's symptoms in a manner such that a lower-level dose was set when the symptoms were relatively light and a higher-level dose was set when the symptoms were relatively heavy. Since the patient's symptoms were relieved just after the initiation of the administration, the administration frequency was once lowered but the patient's symptoms exacerbated, resulting in an increment of the administration frequency to allow to continue the administration. As a result, after two months from the initiation of the administration, the patient's symptoms observed previously were totally relieved, and the patient recovered up to be able to work with a sense of fulfillment. In this application no side effects were induced by the supplemental health food.

Example for application 2

Méniére's Disease

A 45-year-old female patient, who was diagnosed with Méniére's disease, who had been suffering from dizziness, insomnia, muscle stiffness of the shoulder, and diarrhea as main symptoms, and who was almost incapable of conducting household, was administered with the supplemental health food at a dose of about one gram per shot and a maximum administration frequency of up to 15 shots per day. The administration frequency was allowed for the conditions of the patient's symptoms in a manner such that a lower-level dose was set when the symptoms were relatively light and a higher-level dose was set when the symptoms were relatively heavy. The symptoms of the patient were shortly relieved just after the initiation of the administration, and the patient recovered up to be able to conduct household sufficiently. In this application no side effects were induced by the supplemental health food.

Example for application 3

Neurasthenia

A 33-year-old female patient, who was diagnosed with neurasthenia, who had been suffering from systemic malaise, insomnia, and enervation as main symptoms, and who had been administered with an antianxiety drug and a drug for psychoneuroses prescribed by the mental department of a hospital, was administered with the supplemental health food at a dose of about one gram per shot and an adequate administration frequency of up to 10 shots per day. The administration frequency was allowed for the degree of patient's symptoms in a manner such that a lower-level dose was set when the symptoms were relatively light and a higher-level dose was set when the symptoms were relatively heavy. One-month after the initiation of the administration, the patient recovered to a condition of that she could perceive herself the reduction of enervation, and three-months after the initiation of the administration, she recovered to a level that she could energetically work. In this application no side effects were induced by the supplemental health food.

The above three Examples of application indicate that the present neuro-function regulatory agent comprising glycosyl vitamin P recovers the disordered and defected neuro-functions to the normal condition with lesser side effects, and that the present agent exerts a remarkable effect on relieving loss of appetite, insomnia, emotional disturbance, malaise, ease feeling to fatigue, feeling of anxiety, emotional instability, ataxia, paresthesia, lalopathy, paralysis, headache, dizziness, nausea, diarrhea, palpitation, muscle stiffness of the shoulder, lumbago, etc., all of which are accompanied by nerve diseases.

With reference to the following Examples, the preferred embodiments according to the present invention are described in the below:

EXAMPLE 1
Health Food

One hundred and fifty parts by weight of "TREHASTAR®", a trehalose syrup commercialized by Hayashibara Shoji, Inc., Okayama, Japan, was heated and concentrated in vacuo up to give a moisture content of about 15 w/w %. The concentrate was mixed with a solution obtained by dissolving 13 parts by weight of gelatin in 18 parts by weight of water, one part by weight of "αG HESPERIDIN H" with a total hesperidin content of 22–26%, a glycosyl hesperidin powder commercialized by Hayashibara Shoji, Inc., Okayama, Japan, two parts by weight of citric acid, and adequate amounts of a coloring agent and a flavor, and the resulting mixture was shaped and packed into a gummy candy.

The product with a satisfactory texture and flavor is useful as a health food that improves/maintains the normal neuro-function or prevents nerve diseases.

EXAMPLE 2
Health Food

Three parts by weight of a gum base was melted by heating until softened, mixed with seven parts by weight of "NUMIX®", a powdered green and yellow vegetable with a trehalose content of about 50 w/w %, commercialized by H+B Life Science Co., Ltd., Okayama, Japan; adequate amounts of a coloring agent and a flavor; and "αG RUTIN P", a glycosyl rutin powder with a total rutin content of 40–46%, d.s.b., in an amount sufficient to be brought up to a content of 0.1%, d.s.b., and the resulting mixture was in usual manner kneaded, shaped, and packed to obtain a chewing gum containing glycosyl vitamin P.

The product with a satisfactory texture and taste is useful as a health food that improves/maintains the normal neuro-function or prevents nerve diseases.

EXAMPLE 3
Health Food

Eighty-six parts by weight of skim milk, three parts by weight of skim milk powder, nine parts by weight of "TREHASTAR®", a trehalose syrup commercialized by Hayashibara Shoji, Inc., Okayama, Japan, 0.1 part by weight of agar, 0.1 part by weight of "αG HESPERIDIN PA", a glycosyl hesperidin powder with a total hesperidin content of 74–78%, d.s.b., commercialized by Hayashibara Shoji, Inc., Okayama, Japan, and 1.8 parts by weight of water were placed in a tank and heated to 55° C. to completely dissolve the contents under stirring conditions. Thereafter, the mixture was homogenized in usual manner, sterilized by a sterilizing cooler, inoculated with 3 w/w % of a starter, injected into a plastic container, and fermented at 37° C. for five hours into a yogurt containing glycosyl vitamin P.

The product with a satisfactory flavor and taste is useful as a health food that improves/maintains the normal neuro-function or prevents nerve diseases.

EXAMPLE 4
Supplemental Health Food

One part by weight of "αG HESPERIDIN PA", a glycosyl hesperidin powder with a total hesperidin content of 74–78%, d.s.b., commercialized by Hayashibara Shoji, Inc., Okayama, Japan, and 99 parts by weight of "TREHAOSE®", a crystalline trehalose powder commercialized by Hayashibara Shoji, Inc., Okayama, Japan, were mixed to homogeneity, and 50 g aliquots of the resulting mixture were injected into glass vials to obtain the desired product.

About one gram of the product is spooned up for direct eating or for drinking after dissolved in water for ease of supplementing an about 10 mg glycosyl vitamin P to the body. The product with a superior solubility and handleability is useful as a supplementary health food that improves/maintains the normal neuro-function or prevents nerve diseases.

EXAMPLE 5
Tablet

Ten parts by weight of "AA-2G", a glycosyl vitamin C powder commercialized by Hayashibara Shoji, Inc., Okayama, Japan, three parts by weight of "αG HESPERIDIN PA", a glycosyl hesperidin powder with a total hesperidin content of 74–78%, d.s.b., commercialized by Hayashibara Shoji, Inc., Okayama, Japan, and 17 parts by weight of "TREHAOSE®", a crystalline trehalose powder commercialized by Hayashibara Shoji, Inc., Okayama, Japan, were mixed to homogeneity. The mixture was tabletted in usual manner to obtain a tablet containing 10 mg glycosyl vitamin P.

The product, having a readily swallowability and solubility and a vitamin C-supplementing action, is useful as a tablet that improves/maintains the normal neuro-function or prevents nerve diseases.

EXAMPLE 6
Solution

In 1,000 parts by weight of distilled water were dissolved six parts by weight of sodium chloride, 0.3 part by weight of potassium chloride, 0.2 part by weight of calcium chloride, 3.1 parts by weight of sodium lactate, 44 parts by weight of "TREHAOSE®", a crystalline trehalose powder commercialized by Hayashibara Shoji, Inc., Okayama, Japan, 1.5 parts by weight of "αG HESPERIDIN PS", a glycosyl hesperidin powder with a total hesperidin content of 80–84%, d.s.b., commercialized by Hayashibara Shoji, Inc., Okayama, Japan, and 0.5 part by weight of "AA-2G®", a glycosyl vitamin C commercialized by Hayashibara Shoji, Inc., Okayama, Japan. The resulting solution was filtered in usual manner, and 25 ml aliquots of the filtrate were injected into plastic containers to obtain a solution containing glycosyl vitamin P.

The product, having an activity of supplementing vitamins, energies, and minerals, is used as an injection for treating nerve diseases.

EXAMPLE 7
Cataplasm

One part by weight of crotamiton and 0.3 part by weight of "αG HESPERIDIN PS", a glycosyl hesperidin powder with a total hesperidin content of 80–84%, d.s.b., commercialized by Hayashibara Shoji, Inc., Okayama, Japan, were heated in a water bath. While dissolving by mixing into a solution, 45.2 parts by weight of distilled water, 10 parts by weight of "TREHAOSE®", a crystalline trehalose powder commercialized by Hayashibara Shoji, Inc., Okayama, Japan, five parts by weight of gelatin, and seven parts by weight of kaolin were placed in a mixer and heated to about 50° C. into a homogeneously dispersed solution. To the solution was added another dispersed solution of 25 parts by weight of glycerine, three parts by weight of sodium polyacrylate, and 3.5 parts by weight of carboxy methyl cellulose. The solution thus obtained was mixed by stirring to obtain a homogeneously-kneaded mixture.

The resulting mixture was added to the above solution and kneaded to homogeneity under stirring conditions. The newly obtained mixture was applied over a nonwoven fabric to form a film with one millimeter thick by using a spreader. After overlaying with a polypropylene sheet one side of the above fabric applied with the solution, the resulting fabric was cut in a prescribed size into the desired product.

The product gives substantially no unsatisfiable feeling when attached to the skin, and the effect lasts for a relatively-long period of time. Thus the product is useful as a cataplasm for treating nerve diseases.

As described above, the present invention was made based on the self-finding that glycosyl vitamin P regulates the human neuro-function within the normal condition. When administered to patients with nerve diseases such as depression, chronic fatigue syndrome, and nervous digestive-diseases, the present agent for regulating the neuro-function exerts a remarkable effect on the relief of loss of appetite, insomnia, emotional disturbance, malaise, feeling of anxiety, emotional instability, ease feeling to fatigue, ataxia, paresthesia, lalopathy, paralysis, headache, dizziness, nausea, diarrhea, palpitation, muscle stiffness of the shoulder, lumbago, etc., all of which are accompanied by nerve diseases. When administered to healthy persons, the present agent exerts a remarkable effect on the relief of feeling of fatigue, ease feeling to fatigue, malaise, loss of appetite, insomnia, and loss of vitality, which are accompanied by social-, physical-, and chemical-stresses.

We claim:

1. A composition for relieving at least one of the conditions of loss of appetite, insomnia, emotional disturbance, malaise, ease feeling to fatigue, feeling of anxiety, emotional instability, ataxia, paresthesia, lalopathy, paralysis, headache, dizziness, nausea, diarrhea, palpitation, muscle stiffness of the shoulder, and lumbago of a subject suffering from at least one of depression, neurosis, Méniére's disease, neurasthenia, chronic fatigue syndrome, nervous digestive-diseases, nervous oastritis, autonomic dystonia, loss of appetite, insomnia, emotional disturbance, malaise, feeling of fatigue, feeling of anxiety, emotional instability, ataxia, paresthesia, lalopathy, paralysis, headache, dizziness, nausea, diarrhea, palpitation, muscle stiffness of the shoulder, lumbago, and loss of vitality, said composition comprising (1) a sufficient amount of glycosyl vitamin P in a unit dosage form for relieving one or more conditions of loss of appetite, insomnia, emotional disturbance, malaise, ease feeling to fatigue, feeling of anxiety, emotional instability, ataxia, paresthesia, lalopathy, paralysis, headache, dizziness, nausea, diarrhea, palpitation, muscle stiffness of the shoulder, and lumbago of said subject, and (2) an amount sufficient of trehalose to promote the activity of said glycosyl vitamin P, together with a carrier for said glycosyl vitamin P, and wherein said carrier is optionally edible.

2. The composition of claim 1, wherein said glycosyl vitamin P is in the form of glycosyl hesperidin, glycosyl rutin, or a mixture thereof.

3. The composition of claim 1, wherein said glycosyl vitamin P is present in an amount of at least 0.001 w/w %.

4. The composition of claim 1, which further contains one or more members selected from the group consisting of food materials, food additives, and pharmaceutically-acceptable carriers for ease of administration of said glycosyl vitamin P.

5. The composition of claim 1, wherein said trehalose is present in an amount of at least five-fold higher than that of said glycosyl vitamin P, on a dry weight basis.

6. The composition of claim 1, which is in an orally or parenterally administrable form.

7. A composition according to claim 1 in the form of a pharmaceutical composition in a unit dosage form suitable for oral or parenteral administration, wherein said carrier is a pharmaceutically acceptable carrier or excipient.

8. The composition of claim 7, wherein said glycosyl vitamin P is in the form of glycosyl hesperidin, glycosyl rutin, or a mixture thereof.

9. The composition of claim 7, wherein said glycosyl vitamin P is present in an amount of at least 0.001 w/w %.

10. The composition of claim 9, wherein said trehalose is present in an amount of at least five-fold higher than that of said glycosyl vitamin P, on a dry weight basis.

11. A method for relieving at least one of the conditions of loss of appetite, insomnia, emotional disturbance, malaise, ease feeling to fatigue, feeling of anxiety, emotional instability, ataxia, paresthesia, lalopathy, paralysis, headache, dizziness, nausea, diarrhea, palpitation, muscle stiffness of the shoulder, and lumbago of a subject suffering from at least one of depression, neurosis, Méniére's disease, neurasthenia, chronic fatigue syndrome, nervous digestive-diseases, nervous oastritis, autonomic dystonia, loss of appetite, insomnia, emotional disturbance, malaise, feeling of fatigue, feeling of anxiety, emotional instability, ataxia, paresthesia, lalopathy, paralysis, headache, dizziness, nausea, diarrhea, palpitation, muscle stiffness of the shoulder, lumbago, and loss of vitality comprising administering to said subject a sufficient amount of a composition comprising
   (1) glycosyl vitamin P as an effective ingredient, and
   (2) an amount sufficient of trehalose to promote the activity of said glycosyl vitamin P, together with a carrier for said composition to relieve at least one of the conditions of loss of appetite, insomnia, emotional disturbance, malaise, ease feeling to fatigue, feeling of anxiety, emotional instability, ataxia, paresthesia, lalopathy, paralysis, headache, dizziness, nausea, diarrhea, palpitation, muscle stiffness of the shoulder, and lumbago of said subject.

12. The method of claim 11, wherein said glycosyl vitamin P is in the form of glycosyl hesperidin, glycosyl rutin, or a mixture thereof.

13. The method of claim 11, wherein said composition is administered to said subject in an amount of at least 0.001 w/w % of said glycosyl vitamin P.

14. The method of claim 11, wherein said trehalose is administered to said subject in an amount of at least five-fold higher than that of said glycosyl vitamin P, on a dry solid basis.

* * * * *